United States Patent [19]

Turney et al.

[11] 4,189,195
[45] Feb. 19, 1980

[54] BATHROOM CABINET

[75] Inventors: Virginia R. Turney; Frank Turney, both of P.O. Box 534, Denison, Tex. 75020; Paul C. Gunn, Fort Worth, Tex.

[73] Assignees: Virginia R. Turney; Frank Turney, both of Dennison, Tex.

[21] Appl. No.: 914,355

[22] Filed: Jun. 12, 1978

[51] Int. Cl.² ............... A61B 19/02; A47B 81/00
[52] U.S. Cl. ................................. 312/209; 312/245; 312/138 R
[58] Field of Search ............... 312/245, 209, 206, 247, 312/248, 138 R, 320; 49/382

[56] References Cited

U.S. PATENT DOCUMENTS

| | | | |
|---|---|---|---|
| 890,194 | 6/1908 | Strong | 312/209 |
| 1,039,877 | 10/1912 | Allan | 312/209 |
| 1,703,859 | 3/1929 | Bauman et al. | 312/245 |
| 1,858,146 | 5/1932 | Ferguson | 312/209 |
| 2,254,431 | 9/1941 | Levine | 312/209 |
| 2,545,089 | 3/1951 | Ladewig | 312/209 |
| 2,880,864 | 4/1959 | Russo | 312/209 |
| 3,219,402 | 11/1965 | Holman | 312/209 |
| 3,524,690 | 8/1970 | Gurney | 312/245 |
| 4,033,650 | 7/1977 | Alissandratos | 312/242 |

*Primary Examiner*—Victor N. Sakran
*Attorney, Agent, or Firm*—Hubbard, Thurman, Turner, Tucker & Glaser

[57] ABSTRACT

A cabinet designed to store feminine hygiene equipment or the like is disclosed. The cabinet includes a frame mountable against a bathroom wall and a cover hinged to one side of the frame for concealing the interior of the cabinet when closed. The frame includes surfaces for supporting a hose in a convoluted manner that achieves complete drainage of the hose into a suitable receptacle at the bottom of the cabinet.

14 Claims, 9 Drawing Figures

BATHROOM CABINET

The present invention pertains generally to bathroom fixtures and more particularly to a cabinet for storing douche equipment or the like.

It is a principal object of the present invention to provide an enclosure mountable against a wall for concealing personal hygiene objects in a convenient manner.

A further and important object of the present invention is to provide a bathroom cabinet for storing a douche bag and hose in a manner that permits the hose to drain completely.

Another object of the present invention is to provide a bathroom cabinet having a frame of molded plastic including integrally formed supports and retainers for storing a hose in a convoluted manner that permits the hose to drain completely in a space much shorter than the overall length of the hose.

The novel features believed to be characteristic of the invention are set forth in the appended claims. The essential features of the invention, however, as well as the above and other objects and advantages will be readily understood upon consideration of the following description of a present preferred embodiment thereof when read with the accompanying illustrations, wherein:

Referring now to the drawings, a presently preferred embodiment of the invention and various modifications thereof will be described in detail, similar reference numerals designating similar parts in the various figures.

Figure 1:
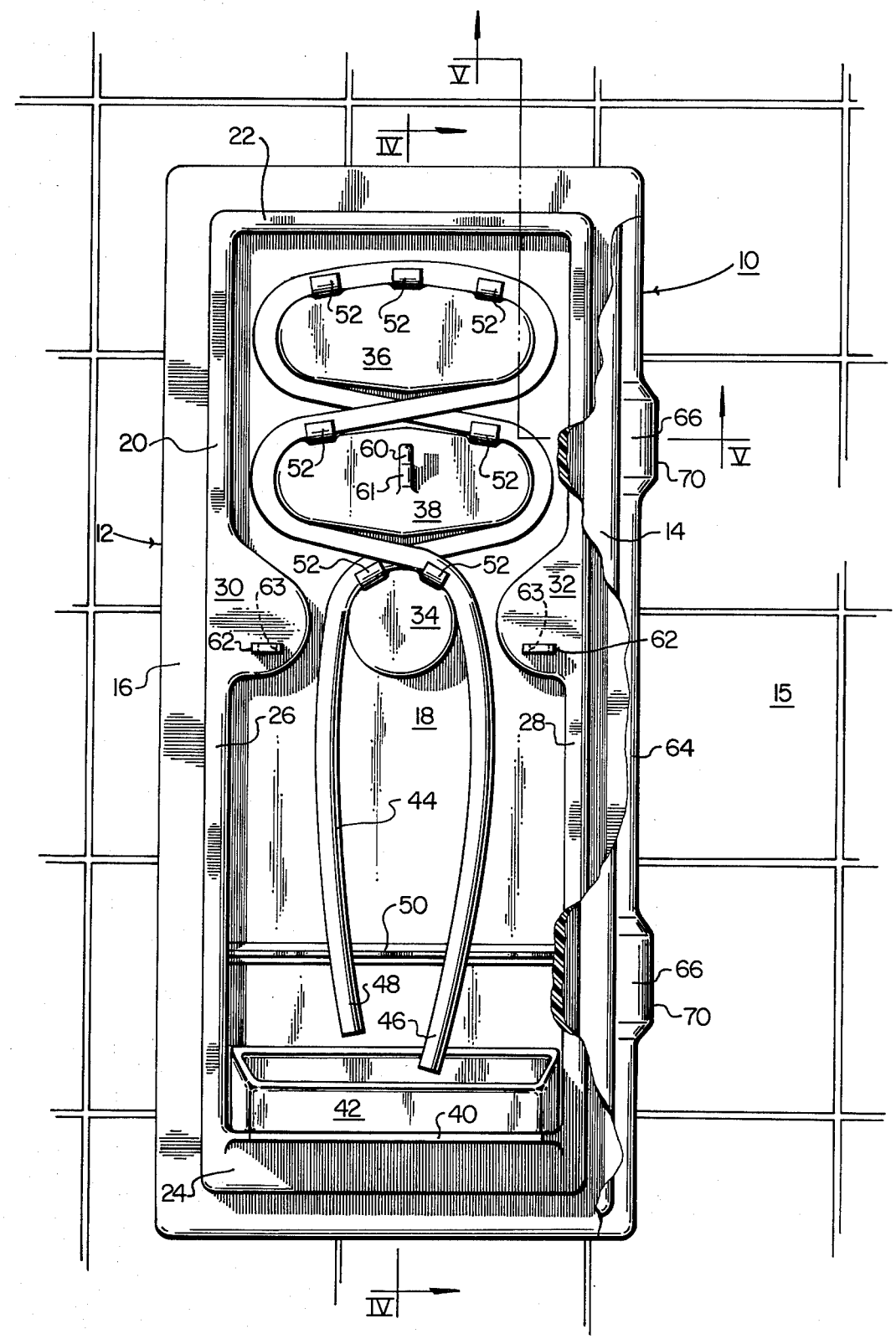
FIG. 1 is a front elevational view of a cabinet in accordance with a preferred embodiment of the invention with portions of a hinged cover broken away to illustrate the interior thereof.
Figure 2:
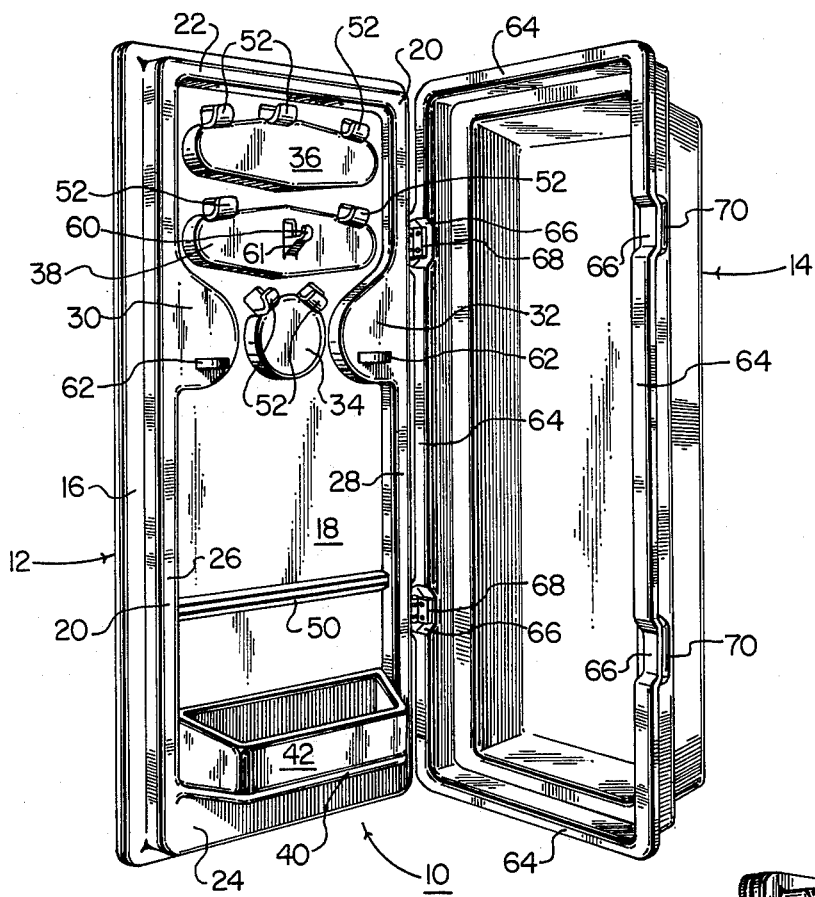
FIG. 2 is a perspective view of the cabinet of FIG. 1 with the cover in an open position.
Figure 3:
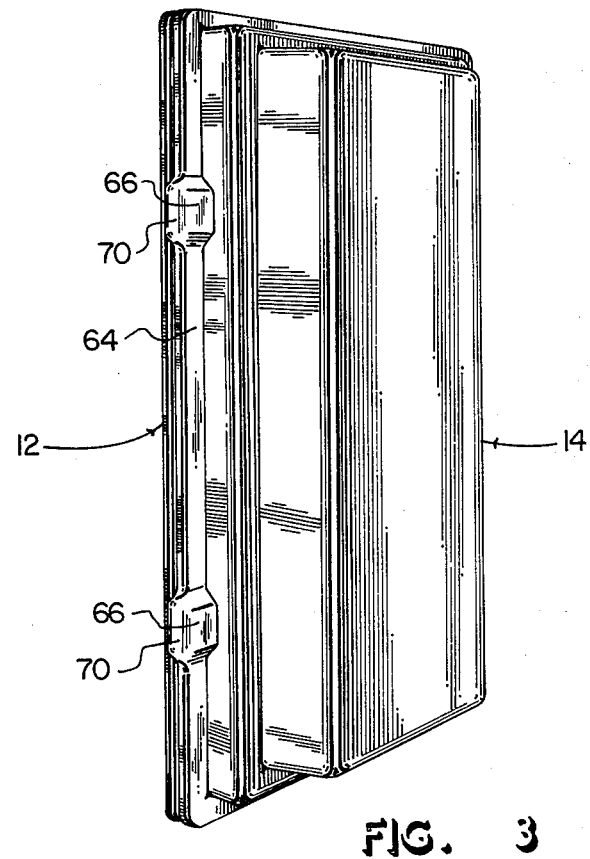
FIG. 3 is a perspective view taken similar to FIG. 2 but with the cover in the closed position.

With particular reference to FIGS. 1-3, a preferred embodiment of the inventive cabinet is illustrated and designated generally by reference numeral 10. The cabinet 10 comprises a frame 12 and a cover 14 pivotally secured to one side of the frame 12. The frame 12 can be mounted against a supporting wall 15, typically a tile bathroom wall, in any conventional manner such as by suitable mechanical fasteners (not shown) at selected points or by a suitable adhesive backing (not shown). As seen in FIGS. 1 and 2, the frame 12 includes a peripheral flange 16, a backwall 18 lying in the same plane as the peripheral flange 16 and a plurality of raised surfaces extending outward from the flange 16 and backwall 18. One of the raised surfaces is a peripheral ridge 20, which includes upper and lower horizontal surface portions 22 and 24 disposed respectively near the top and bottom of the cabinet 10 and vertical surface portions 26 and 28 at the sides thereof. The ridge 20 further includes shoulders 30 and 32 extending transversely toward each other from the side portions 26 and 28, respectively. Additional raised surfaces include a circular rest 34 disposed between the shoulders 30 and 32, and upper and lower oval-shaped rests 36 and 38 disposed between the upper horizontal ridge portion 22 and the circular rest 34. A horizontal shelf 40 extends outwardly from the backwall 18 transversely just above the lower horizontal ridge portion 24. The shelf 40 is adapted to support a suitable fluid receptacle or drip pan 42, which is detachable from the cabinet 10 to facilitate emptying and cleaning.

The above described raised surfaces of the frame 12 permit a hose 44 to be supported in a convoluted manner as specifically illustrated in FIG. 1. In particular, the hose 44 is wrapped around the rests 34, 36 and 38 in a serpentine or crisscross fashion with its ends 46 and 48 projecting downwardly into or just above the receptacle 42. To prevent fluid draining out the hose 44 from running down the backwall 18, an outwardly projecting bar 50 locates the ends 46 and 48 of the hose 44 directly over the receptacle 42. The shoulders 30 and 32 serve to prevent the portions of the hose 44 extending between the lower oval rest 38 and the circular rest 34 from sagging and forming fluid collecting points.

Supporting the hose 44 in such manner permits it to drain completely in a space much shorter than its overall length. A hose having an extended length several times greater than the length of the cabinet 10 can be stored therein and allowed to drain completely provided the hose slopes continuously downward from its uppermost point. In the preferred embodiment illustrated in FIG. 1, the hose 44 drains completely since there is only one point at which the hose 44 is oriented horizontally and that is at its uppermost point above the center of the upper oval-shaped rest 36. From its uppermost point, the hose 44 slopes continuously downward, at first in opposite directions and then through a series of curves so that fluid will run out the ends 46 and 48 without collecting at any point within the hose 44. It will be appreciated that the present invention contemplates a great number of various wrapping arrangements that will permit a hose to drain completely, only one of which is illustrated in FIG. 1. For example, the cabinet 10 could alternatively be provided with a plurality of posts at opposite sides of the frame 12 around which a hose could be weaved in a manner that achieves complete drainage. Furthermore, it will be appreciated that it is not necessary that the hose drain from both ends as in the preferred embodiment described herein, but that one end of the hose could be secured at the top of the cabinet 10 with the other end draining into a suitable receptacle at the bottom. However, an arrangement in which both ends drain at the bottom is preferred as being more effective in reducing the longitudinal space required for storing the hose. Additionally, it will also be appreciated that the cabinet 10 could be modified to support a hose and receptacle in the cover 14 and that the frame 12 could be provided with conventional shelves or storage compartments. All such alternative and modified embodiments are contemplated by the present invention.

In accordance with a unique feature of the present invention, the cabinet 10 preferably includes hose retainers 52 at selected points on the rests 34, 36 and 38. The retainers 52 are preferably integrally formed with the frame 12 by molding plastic or a suitable polymeric material in a conventional manner. It will be appreciated that the hose 44 would tend to slide off the rests 34, 36 and 38 were it not for the retainers 52, particularly when the hose 44 is wet.

Figure 4:
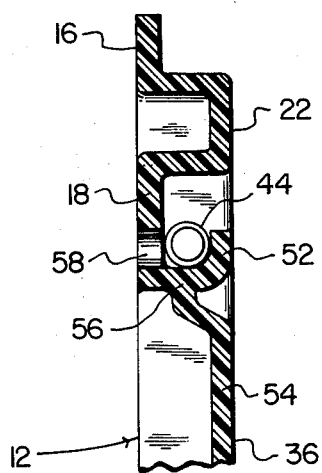
FIG. 4 is a vertical cross section of an upper portion of the cabinet taken along the line IV—IV of FIG. 1 through one of a plurality of hose retainers.

The details of a preferred retainer 52 will now be described with particular reference to FIG. 4. The rest 36 includes a vertical wall 54 and a peripheral wall or edge portion 56 interconnecting the vertical wall 54 and the backwall 18. The retainer 52 shown in FIG. 4 curves upward from a point along the edge 56 into the same plane as the vertical wall 54 in a manner typical of each of the retainers 52 shown in FIGS. 1 and 2. Thus, the retainers 52 provide slots or grooves along the upper peripheral surfaces of the rests 34, 36 and 38 for receiving and holding the hose 44 in place. Those skilled in the art will appreciate that the retainers 52 can be molded using die inserts, each of which leave a hole 58 registered behind each retainer 52.

Using similar molding techniques, a hook 60, which preferably extends outward from the oval rest 38 as seen best in FIG. 2, can be integrally formed with the frame 12. The hook 60 preferably has a lower surface 61 that slopes downward from the outer portion of the hook 60 to the adjoining vertical wall of the rest 38 to provide added strength for supporting a water bottle or bag (not shown).

An additional feature of the preferred embodiment is the provision of a nozzle carrier 62 extending outwardly from the vertical surface of each of the shoulders 30 and 32 as seen in FIGS. 1 and 2. Each carrier 62 has a cylindrical aperture 63 having a vertical axis permitting a nozzle (not shown) of the type employed with conventional douche equipment to be supported therein in a manner that allows drippings from the nozzle to fall into the fluid receptacle 42. Presently, the carriers 62 are preferably formed separately from the frame 12 and attached thereto in a suitable manner as by means of thread fasteners (not shown) extending through the vertical walls of the shoulders 30 and 32. It will be appreciated, however, that similar carriers or equivalent means for supporting nozzles could alternatively be integrally molded with the frame 12.

Referring again to FIGS. 2 and 3, additional unique features of the preferred cabinet 10 will now be described. The cover 14 is provided with a peripheral flange 64 adapted to rest against the frame's peripheral flange 16 when the cabinet 10 is closed. Cup-shaped portions 66, which serve either as handles or hinge-mounting areas, are provided at four locations in the vertical side portions of the flange 64. The cover 14 is preferably symmetrical about a longitudinal center line with two of the cup-shaped portions 66 on each side. Such symmetry is not only aesthetically desirable but also enables the cover 14 to be hinged at either side to the frame 12. FIG. 2 specifically illustrates the version of the cabinet 10 with hinges 68 secuurring the cover 14 to the right side of the frame 12 as viewed from the front. As will be appreciated best from the view of FIG. 3, each cup-shaped portion 66 includes a laterally extending portion 70 which projects beyond the edge of the flange 16 when the cover 14 is closed against the frame 12. The extensions 70 serve as handles for grasping and opening the cover 14 by slipping one's fingertips behind one of the extensions 70 at the non-hinged side of the cabinet 10.

Figure 5:
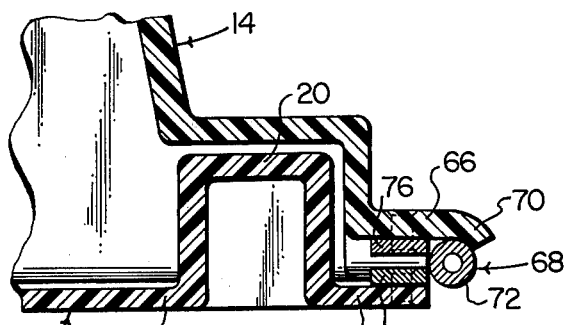
FIG. 5 is a horizontal cross section through a portion of the cabinet including a hinge taken along line V—V of FIG. 1.
Figure 6:
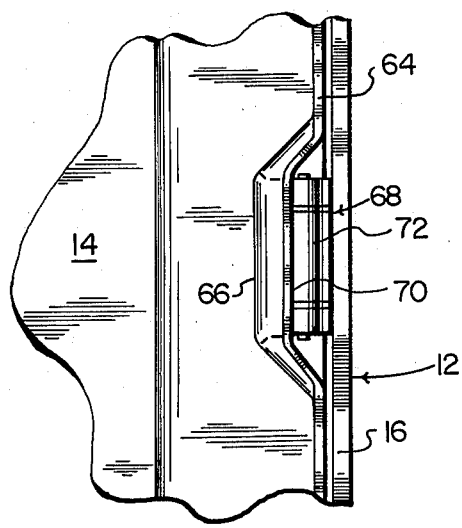
FIG. 6 is an enlarged fragmentary side elevation illustrating the hinge area of the cabinet.

An additional aesthetic feature of the cabinet 10 is that the extensions 70 of the cup-shaped portions 66 conceal the hinges 68 from view when the cover 14 is closed as will be appreciated from the views of FIGS. 5 and 6. In particular, the preferred hinge 68 includes a conventional barrel 72 with pivotally attached wings 74 and 76 which can be secured in standard fashion to the flanges 16 and the cup-shaped portion 66, respectively, as shown in FIG. 5.

Figure 7:
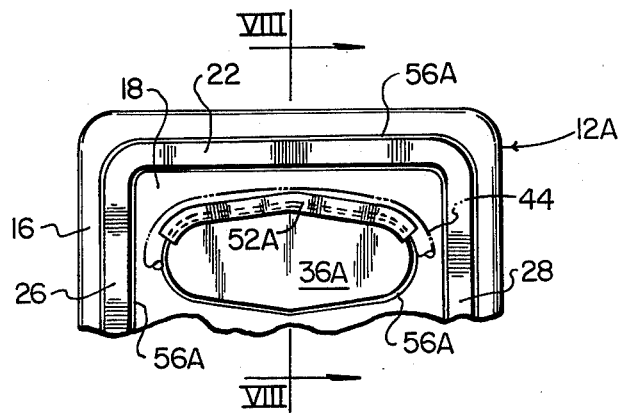
FIG. 7 is a front elevation of an upper portion of a modified cabinet embodiment in accordance with the present invention.
Figure 8:
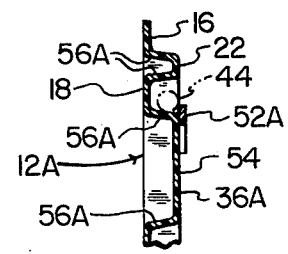
FIG. 8 is a vertical cross section taken along line VIII—VIII of FIG. 7.

Now referring to FIGS. 7 and 8, a modified frame 12A will be described. The parts of the modified frame 12A that are similar to parts of the previously described frame 12 are denoted by the same reference numerals. The modified features of the frame 12A include a separately formed retainer 52A which is secured along the upper edge of a modified hose rest 36A. Additionally, the raised surfaces of the modified frame 12A are expressly illustrated with peripheral walls 56A that are slightly tapered so that they converge gradually in moving outward from the backwall 18. It will be appreciated that tappering the peripheral walls in such manner facilitates removal of the frame 12A from its mold. It is to be understood that similar modified retainers and rests are provided in the unseen portion of the frame 12A which except for the modifications is otherwise similar to the previously described frame 12. The retainer 52A conforms to the sloping contour of the rest 36A and projects slightly above and continuously along the top edge of the rest 36A to provide a slot between the backwall 18 and the upper edge of the retainer 12A for receiving and holding the hose 44 in place as shown phantom.

Figure 9:
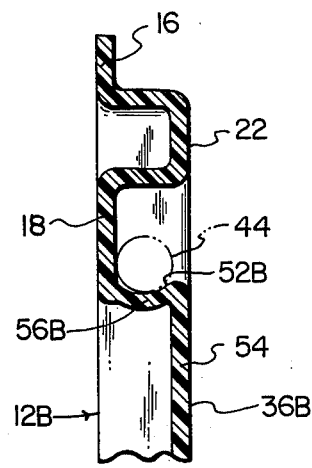
FIG. 9 is a vertical cross section similar to FIG. 8 illustrating another modified cabinet embodiment in accordance with the present invention.

Another modified frame 12B is illustrated in FIG. 9, previously described similar parts retaining the same reference numerals. The upper peripheral wall 56B of the rest 36B is curved slightly to provide a grooved surface 52B for retaining the hose 44 in place on the rest 36B. In order to avoid using complex molding techniques, the grooved wall 56B can be provided by deforming the plastic after it is released from the mold. If such a deforming technique is used, a suitable thermoplastic material should be employed. Examples of suitable thermoplastic materials include polystyrene, polyvinylchloride, polyethylene, ABS polymers and known equivalents.

Although a preferred embodiment and modifications thereof have been described in detail, it is to be understood that additional modifications and substitutions can be made and various alternative embodiments produced in accordance with the invention without departing from the spirit and scope thereof as defined by the appended claims.

What is claimed is:

1. A cabinet for storing and concealing personal hygiene objects including a fluid conducting hose, the cabinet comprising:

a frame mountable against a vertical supporting wall and a cover adapted to be pivotally secured to the frame, the frame including a back wall and a plurality of raised surfaces extending outward from the backwall, the frame further including means for supporting a receptacle in a lower portion of the cabinet for receiving the fluid drainage from the hose, the raised surfaces including an oval-shaped rest for supporting the hose in an upper portion of the frame and at least a second rest disposed between the oval-shaped rest, and the receptacle supporting means, the oval-shaped rest and the second rest being adapted to permit the hose to be wrapped around their peripheral edges in a convoluted manner whereby the hose can be stored in a space much shorter than the overall length of the hose while simultaneously allowing the hose to drain completely from both ends into the receptacle.

2. A cabinet for storing and concealing personal hygiene objects including a fluid conducting hose, the cabinet comprising:

a frame mountable against a vertical supporting wall and a cover adapted to be pivotally secured to the frame, the frame including a backwall and a plurality of raised surfaces extending outward from the backwall, the raised surfaces including a first rest disposed in an upper portion of the frame for supporting the hose therefrom and at least a second rest disposed below the first rest, the rests being adapted to permit the hose to be wrapped around their peripheral edges in a convoluted manner whereby the hose can be stored in a space much shorter than the overall length of the hose while simultaneously allowing the hose to drain completely, wherin the rest are adapted so that the hose can be wrapped substantially around the entire periphery of at least the first rest so that the hose crosses itself between the first and second reste in a manner that permits the entire hose to drain completely from both ends, the first rest being further adapted to support the hose so that it slopes continuously downward from its uppermost point, whereby the hose is tangential to the horizontal only at said uppermost point.

3. The cabinet of claim 2 wherein the frame comprises a unitary construction of molded polymeric material.

4. The cabinet of claims 2 or 3 further comprising means secured to the upper periphery of the rests for retaining the hose in place on the rests.

5. The cabinet of claim 3 further comprising means integrally formed with the frame at the upper periphery of the rests for retaining the hose in place on the rests.

6. The cabinet of claim 3 wherein the cover comprises a unitary contruction of molded polymeric material and wherein the cover includes generally cup-shaped portions along side edges thereof for concealing hinges.

7. The cabinet of claim 6 wherein the cover is symetrical about a longitudinal center line such that there are at least two generally cup-shaped portions on each side of the cover, and wherein the generally cup-shaped portions include portions extending laterally outward from the edge of the cabinet to provide handle means for grasping the edge of the cover on the non-hinged side to permit opening of the cover.

8. The cabinet of claim 2 wherein the first and second rests are oval-shaped and the long axis of each of said oval-shaped rests is oriented transversely with respect to said frame.

9. The cabinet of claim 8 wherein said frame further includes a circular-shaped rest disposed below the oval-shaped rests.

10. The cabinet of claim 9 wherein the frame further includes a peripheral ridge having shoulders at opposite sides of the circular rest for perventing the hose from sagging in the regions where the ends of the hose extend between the lower oval rest and the circular rest when the hose is wrapped around the rests so that it crosses itself between adjacent rests.

11. The cabinet of claim 10 further comprising means extending out from at least one of the shoulders for carrying a nozzle in a manner that permits the nozzle to drain.

12. The cabinet of claim 10 wherein the frame further includes means below the circular rest for preventing the ends of the hose from touching the backwall.

13. The cabinet of claim 10 further comprising means extending outward from one of the rests for hanging a water bottle, bag or the like within the cabinet.

14. The cabinet of claim 3 wherein the raised surfaces have tapered peripheral walls to facilitate releasing the frame from its mold.

* * * * *